United States Patent
Inukai et al.

(10) Patent No.: US 7,179,933 B2
(45) Date of Patent: Feb. 20, 2007

(54) PREPARATION OF ORGANOHALOSILANES

(75) Inventors: Tetsuya Inukai, Annaka (JP); Hajime Ishizaka, Annaka (JP); Mikio Aramata, Annaka (JP); Yukinori Satou, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/081,691

(22) Filed: Mar. 17, 2005

(65) Prior Publication Data

US 2005/0209475 A1    Sep. 22, 2005

(30) Foreign Application Priority Data

Mar. 18, 2004 (JP) ............................. 2004-077901

(51) Int. Cl.
- C07F 7/04 (2006.01)
- C07F 7/08 (2006.01)
- C07F 7/16 (2006.01)

(52) U.S. Cl. .................................................. 556/472
(58) Field of Classification Search ................ 556/472
    See application file for complete search history.

(56) References Cited

U.S. PATENT DOCUMENTS

| | | | |
|---|---|---|---|
| 2,380,995 A | 8/1945 | Rochow et al. | |
| 4,500,724 A | 2/1985 | Ward, III et al. | |
| 4,602,101 A | 7/1986 | Halm et al. | |
| 5,059,706 A | 10/1991 | Degen et al. | |
| 6,005,130 A | 12/1999 | Lewis et al. | |
| 6,025,513 A * | 2/2000 | Nakanishi et al. | 556/472 |
| 6,215,012 B1 * | 4/2001 | Ueno et al. | 556/472 |
| 6,218,562 B1 * | 4/2001 | Aramata et al. | 556/472 |
| 6,242,629 B1 * | 6/2001 | Ueno et al. | 556/472 |
| 6,288,258 B1 | 9/2001 | Aramata et al. | |
| 6,365,766 B1 | 4/2002 | Aramata et al. | |
| 6,395,917 B1 * | 5/2002 | Ishizaka et al. | 556/472 |
| 6,506,923 B2 | 1/2003 | Inukai et al. | |
| 6,686,312 B1 | 2/2004 | Aramata et al. | |

FOREIGN PATENT DOCUMENTS

| | | |
|---|---|---|
| JP | 5-51596 B2 | 8/1993 |
| JP | 6-92421 B2 | 11/1994 |
| JP | 2000-254506 A | 9/2000 |
| JP | 2000-296334 A | 10/2000 |
| JP | 2001-122880 A | 5/2001 |
| JP | 2002-241384 A | 8/2002 |

OTHER PUBLICATIONS

Komitsky et al., "The influence of promotoer levels on the direct synthesis", Silicon for the Chemical Industry IV, Geiranger, Norway (1998), pp. 217-225.

Rosch et al., "The starting phase of the MCS-direct synthesis, some experimental observations", Silicon for the Chemical Industry III, Sandefjord, Norway (1996), pp. 269-273.

Lainer et al., "A method for obtaining dimethyldichlorosilane", USSR Application Specification No. 617,569, Certificate of inventorship No. 122,749, Jan. 24, 1959.

Lobusovich et al., "A method to produce methylchlorosilanes", USSR Application Specification No. 903,369, Certificate of inventorship No. 178,817, Mar. 11, 1966.

Lobusovich et al., "Method for prodcution of alkylchlorsilanes", USSR Application Specification No. 1,152,943, Certificate of inventorship No. 237,892, Nov. 20, 1969.

* cited by examiner

Primary Examiner—Thurman K. Page
Assistant Examiner—Chukwuma Nwaonicha
(74) Attorney, Agent, or Firm—Birch, Stewart, Kolasch & Birch, LLP

(57) ABSTRACT

Organohalosilanes are prepared by reacting metallic silicon particles with an organohalide in the presence of a copper catalyst. A contact mass composed of the metallic silicon and the copper catalyst contains an effective amount of a catalyst alloy containing 0.2–8 wt % of tin and 4–20 wt % of phosphorus which is powdered by atomization.

5 Claims, No Drawings

PREPARATION OF ORGANOHALOSILANES

CROSS-REFERENCE TO RELATED APPLICATION

This non-provisional application claims priority under 35 U.S.C. §119(a) on Patent Application No. 2004-077901 filed in Japan on Mar. 18, 2004, the entire contents of which are hereby incorporated by reference.

This invention relates to an industrial process for preparing organohalosilanes.

BACKGROUND OF THE INVENTION

With respect to the synthesis of alkylhalosilanes, Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silane product and a T/D ratio.

Organohalosilane products contain diorganodihalosilane (D), triorganohalosilane (M), organotrihalosilane (T), etc. as well as by-products such as organohydrodihalosilane (H) and organohalodisilane. In particular, disilanes are known as a high-boiling fraction among silicone manufacturers using direct method organohalosilanes because few processes are available for the effective utilization of disilanes, and most disilanes are discarded as residues. The T/D ratio is a compositional ratio of organotrihalosilane to diorganodihalosilane in the entire organohalosilanes produced, with a lower T/D ratio being preferred. The formation rate of organohalosilane is represented by a space time yield (STY) which is the weight of crude organohalosilane produced per unit time relative to the weight of metallic silicon held in the reactor. In order to improve the content of diorganohalosilane produced, reduce the T/D ratio or increase the STY, various research works have been made with a focus on the catalyst and co-catalyst.

USSR Application Specification No. 617,569 (Certificate of inventorship No. 122,749) dated Jan. 24, 1959 discloses reaction in the presence of metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 6-92421 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated Feb. 6, 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122, 749). Also USSR Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this US patent are improved over the last-mentioned USSR patent, there still remain many problems including hazard imposed by spontaneously igniting elemental phosphorus and increased cost of raw materials. Then this US patent is also unsuitable to apply to commercial scale reactors. Also, F. Komitsky et al., Silicon for the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration. U.S. Pat. No. 6,025,513 intends to add boron to a contact mass wherein the boron concentration is controlled so as to improve productivity. U.S. Pat. No. 5,059,706 discloses to introduce a phosphorus compound in a vapor phase into a reactor for increasing selectivity. U.S. Pat. No. 6,005,130 discloses to introduce organomonophosphine for increasing selectivity.

However, the phosphorus base additives used in the prior art have an outstanding trade-off between activity and composition selectivity. In particular, it is pointed out that oxide originating from phosphorus can exacerbate flow on the particle surface. Therefore, the conventional phosphorus base additives offer few merits on the continuous operation of commercial scale reactors. Other additives are known from L. Rosch, W. Kalchauer et al., Silicon for the Chemical Industry IV, Sandefjord, Norway (1996) wherein monomethyldichlorosilane is introduced for improving activity. This additive is effective only at the initial period, but not regarded as exerting a lasting effect during the continuous operation of commercial scale reactors.

While most prior art proposals focus on the elements of which the catalyst is made, as found in the foregoing references, some proposals to improve catalysis have recently been made from a brand new point of view. For example, U.S. Pat. No. 6,686,312 (corresponding to JP-A 2000-254506) discloses the use of a thermally active metallic copper powder having a large quantity of strain energy; and U.S. Pat. No. 6,365,766 (corresponding to JP-A 2000-296334) discloses the use of a copper powder in the form of flakes or scales, both for industrially advantageous preparation of organohalosilanes. The inventors proposed in U.S. Pat. No. 6,288,258 (corresponding to JP-A 2001-122880) efficient preparation of organohalosilanes at a reduced T/D ratio of trioganohalosilane to diorganodihalosilane by adding phosphor bronze to the catalyst.

These organohalosilane synthesis reactions are gas-solid heterogeneous reactions in fluidized beds, stirred beds or fixed beds. The results of reaction largely depend on the powder behavior of the contact mass or catalyst. In particular, the industrial process uses an excess of a copper catalyst or co-catalyst, allowing particles to agglomerate together within the contact mass to interfere with the flow of the contact mass and detract from productivity. To solve these problems, the inventors intended to establish a catalyst system in which both the chemical action and powder properties of a powdered catalyst contribute to improved productivity, and proposed to prepare organohalosilanes using a catalytic metal or alloy powder as atomized, which matured to U.S. Pat. No. 6,506,923 (corresponding to JP-A 2002-241384).

SUMMARY OF THE INVENTION

An object of the invention is to provide a novel and improved process for preparing organohalosilanes at a drastically increased formation rate.

The inventors extended research works on the catalysis of phosphor bronze and the compatibility of catalysis with powder properties. As a result, the inventors have found that a catalyst alloy powder containing 0.2 to 8% by weight of tin and 4 to 20% by weight of phosphorus which is powdered by atomization is effective for improving the production of organohalosilanes over time.

More particularly, to overcome actual drawbacks found when the direct method or Rochow method is carried out, for example, the drawback that the industrial process uses an excess of a copper catalyst or co-catalyst, allowing particles to agglomerate together within the contact mass to interfere with the flow of the contact mass and detract from productivity, the inventors intended to establish a catalyst system which meets all the requirements including the chemical action and fluidity of a powdered catalyst and the fluidity of a contact mass. As a result, the inventors have reached an organohalosilane producing process using a contact mass containing an effective amount of a catalyst alloy powder containing 0.2 to 8% by weight of tin and 4 to 20% by weight of phosphorus which has been produced by an atomizing technique.

Specifically, it has been found that the rate of useful silane formation is improved by adding an atomized catalyst alloy powder containing 0.2 to 8% by weight of tin and 4 to 20% by weight of phosphorus, rather than a resinous powder by electrolytic technique, an angular or fragmental powder by stamping or grinding technique, a powder by heat treatment, and a flaky or microcrystalline powder by chemical reduction. The inventors presumed that in designing the function of a catalyst for use in the direct method, how to prepare a catalyst powder largely governs the powder properties of the catalyst powder and a contact mass containing the same. Since the atomizing technique produces a powder containing more spherical particles, the inventors have applied a catalyst powder as atomized to the direct method.

It is noted that the commercial phosphor bronze commonly used in the art is divided into the following three groups:
(1) Ordinary bronze is deoxidized with P, with little P left.
(2) Bronze with less than 10% Sn is deoxidized with P, with a small amount of P left.
(3) To bronze with more than 10% Sn is added 0.3–1.5% P. Mainly cast, and used as bearings, etc.

In these conventional alloys, the Sn concentration is higher than the P concentration by one or more orders. If such an alloy is used as the catalyst, it is very difficult to maintain a balance between the concentrations and actions of elements in the reactor.

By contrast, the inventors challenged to use a catalyst alloy whose composition differs significantly from the existing phosphor bronze, that is, a catalyst alloy containing 0.2 to 8% by weight of Sn and 4 to 20% by weight of P. By using a catalyst alloy of such a unique composition and powdering it by atomization, the inventors succeeded in improving the productivity of an organohalosilane preparing process and its longevity.

The process of the present invention that uses in the direct method a catalyst alloy containing 0.2 to 8% by weight of tin and 4 to 20% by weight of phosphorus which is powdered by atomization is adapted to form a contact mass containing a trace, but effective amount of spherical particles, to improve the fluidity of particles within the contact mass, and to improve the rate of formation of useful silane and its longevity. In this sense, the present invention is based on a different concept from the past improvements which rely on the short-lived action of catalysts. Based on this concept, the inventors studies a series of catalytic metal powders as processed by various atomizing techniques and attempted to synthesize organohalosilanes by reacting metallic silicon with an organohalide in the presence of metallic copper or a copper compound catalyst such as copper chloride, copper oxide or copper acetate and optionally, a co-catalyst like metallic zinc, zinc-copper alloys or zinc compounds such as zinc chloride, zinc oxide or zinc acetate; metallic tin, lead-copper alloys or tin compounds such as tin chloride or tin oxide; metallic antimony or antimony compounds such as antimony chloride or antimony oxide; metallic aluminum or aluminum compounds such as aluminum chloride or aluminum oxide; metallic phosphor, inorganic phosphorus compounds such as phosphorus trichloride or phosphorus oxide, monoalkylphosphines such as trimethylphosphine or triphenylphosphine, or polyorganophosphine compounds such as organic diphosphines. The inventors have discovered that the use of a contact mass containing an effective amount of a catalyst alloy powder containing 0.2 to 8% by weight of tin and 4 to 20% by weight of phosphorus which is powdered by atomization is effective in improving the rate of formation of organohalosilanes and increasing the yield of silicon reaction without reducing the proportion of useful silane. It is emphasized that the use of a contact mass containing an effective amount of a catalyst alloy powder containing 0.2 to 8% by weight of tin and 4 to 20% by weight of phosphorus which is powdered by atomization is successful in achieving a markedly increased rate of formation of organohalosilanes without a substantial change in the useful silane content.

The present invention provides a process for preparing organohalosilanes having the general formula (I):

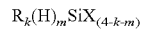

$R_k(H)_m SiX_{(4-k-m)}$ wherein R is a monovalent hydrocarbon group of 1 to 12 carbon atoms, X is a halogen atom, k is an integer of 1 to 3, m is an integer of 0 to 2, and the sum of k+m is 1 to 3, by reacting metallic silicon particles with an organohalide in the presence of a copper-containing catalyst. A contact mass composed of the metallic silicon and a copper-containing catalyst component contains an effective amount of a catalyst alloy containing 0.2 to 8% by weight of tin and 4 to 20% by weight of phosphorus which is powdered by atomization.

The atomization is typically a gas atomization, vacuum atomization, water atomization, centrifugal atomization, rotating electrode or rotating coolant fluid technique.

In preferred embodiments, the catalyst alloy is a copper alloy; the powdered catalyst alloy has an average particle size of 1 to 200 μm; the powdered catalyst alloy has a specific surface area of 0.01 to 1.0 m²/g as measured by the BET or air permeability method.

Also preferably, the catalyst component comprises metallic copper or a copper compound and optionally a co-catalyst selected from the group consisting of metallic zinc, zinc compounds, metallic tin, tin compounds, metallic antimony, antimony compounds, metallic aluminum, aluminum compounds, metallic phosphorus and phosphorus compounds.

In the preparation of organohalosilanes, the use of a contact mass containing an effective amount of a catalyst alloy containing 0.2 to 8% by weight of tin and 4 to 20% by weight of phosphorus which is powdered by atomization is successful in achieving a markedly increased rate of formation of organohalosilanes, its longevity, and an increased yield of silicon reaction without a lowering in selectivity of useful silane.

DESCRIPTION OF THE PREFERRED EMBODIMENTS

The process for preparing organohalosilanes according to the invention involves the step of reacting metallic silicon particles with an organohalide in the presence of a copper-containing catalyst to thereby form organohalosilanes of the following general formula (I):

$$R_k(H)_m SiX_{(4-k-m)} \quad (I)$$

wherein R is a monovalent $C_1$–$C_{12}$ hydrocarbon group, X is a halogen atom, k is an integer of 1 to 3, m is an integer of 0 to 2, and k+m is an integer of 1 to 3.

The process of the invention can be carried out in any of fixed bed reactors, stirred bed reactors and fluidized bed reactors. From the industrial aspect, a fluidized bed reactor suited for continuous operation is advantageously employed.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 μm, corresponding to 50% of the weight base cumulative size distribution curve on sieving, in order that the metallic silicon powder have good fluidity.

The organohalides to be reacted with metallic silicon to form organohalosilanes are preferably of the following general formula (II):

$$RX \quad (II)$$

wherein R is a monovalent hydrocarbon group of 1 to 12 carbon atoms, preferably 1 to 6 carbon atoms. Examples of R include aryl groups such as phenyl and tolyl, aralkyl groups such as benzyl, phenylethyl and phenylpropyl, alkenyl groups such as vinyl, allyl, propenyl and butenyl, and alkyl groups such as methyl, ethyl, propyl, butyl and hexyl. X is a halogen atom, typically chlorine or bromine. Illustrative of suitable organohalides are methyl chloride, ethyl chloride, propyl chloride, methyl bromide, ethyl bromide, benzene chloride and benzene bromide. Of these, methyl chloride and benzene chloride are preferable in the industry. Methyl chloride is most useful because dimethyldichlorosilane produced therefrom finds a wide variety of applications as the raw material for many silicone resins. The organohalide is previously heated and gasified before it is fed into the reactor. The organohalide gas may be fed alone or along with an inert gas in a sufficient amount to fluidize the contact mass. The fluidizing amount is determined as appropriate from the diameter of the reactor and the superficial velocity.

In the reaction of metallic silicon with organohalosilanes, there is added a copper-containing catalyst, simply referred to as copper catalyst. The copper catalyst may be selected from various forms of copper including elemental copper (or metallic copper) such as powdered copper and stamped copper, and copper compounds such as cuprous oxide, cupric oxide, copper halides (e.g., copper chloride) and copper acetate. Any of promoters such as zinc, tin, antimony, and arsenic may be used as the co-catalyst. The co-catalyst may be used alone or in the form of an alloy with copper. Suitable combinations of the copper catalyst with the co-catalyst are copper alloys including Cu—Zn, Cu—Sn, and Cu—Zn—Sn (or Sb or As). Examples of the other co-catalyst include metallic zinc, zinc compounds such as zinc chloride, zinc oxide, and zinc acetate, metallic tin, tin compounds such as tin chloride and tin oxide, metallic antimony, antimony compounds such as antimony chloride and antimony oxide, metallic aluminum, aluminum compounds such as aluminum chloride and aluminum oxide, metallic phosphorus, inorganic phosphorus compounds such as phosphorus trichloride and phosphorus oxide, monoalkylphosphines such as trimethylphosphine and triphenylphosphine, and polyorganophosphine compounds such as organic diphosphine compounds. Any of these copper catalysts may be admitted alone into the reactor.

An appropriate amount of the copper catalyst charged is about 0.1 to 10 parts, and more preferably about 2 to 8 parts by weight, calculated as copper, per 100 parts by weight of the metallic silicon powder. Also the co-catalyst is used in an effective amount which is determined depending on its identity. Specifically, zinc is used in an amount of 0.05 to 1 part by weight per 100 parts by weight of the metallic silicon powder; tin, antimony or arsenic, alone or in combination, is used in a (total) amount of 0.001 to 0.05 part, especially 0.005 to 0.01 part by weight per 100 parts by weight of the metallic silicon powder.

According to the invention, an effective amount of a catalyst alloy powder containing 0.2 to 8% by weight of tin and 4 to 20% by weight of phosphorus which is powdered by atomization is added to a contact mass composed of the above-described metallic silicon and copper-containing catalyst component before reaction between metallic silicon and an organohalide is carried out.

When a catalyst alloy powder is produced by atomization, the preferred catalyst alloy is a copper alloy, brass, bronze, or a catalyst alloy containing two or more elements selected from among copper, zinc, tin, phosphorus, nickel, cobalt, iron, manganese, chromium, tungsten, molybdenum, boron, silicon and carbon. Of these, the more preferred catalyst alloy is a copper alloy containing tin and phosphorus.

The catalyst alloy in powder form should have a tin content of 0.2 to 8% by weight, preferably 0.3 to 7% by weight, and a phosphorus content of 4 to 20% by weight, preferably 6 to 18% by weight. The content of tin and phosphorus combined is preferably 5 to 25% by weight, more preferably 6 to 20% by weight. The balance is composed of copper and the above-mentioned elements other than tin and phosphorus. Preferably the balance is copper, with copper accounting for 75 to 95%, more preferably 80 to 94% of the catalyst alloy. If the contents of tin and phosphorus are outside the ranges, the resulting contact mass may allow for a more proportion of by-products, failing to maintain a rate of formation of organohalosilane.

The catalyst alloy powder is produced by atomization. The term "atomization" as used herein refers to a technique of quenching a molten metal or alloy to produce fine drops or particles. The atomization is typically selected from among gas atomization, vacuum atomization, water atomization, centrifugal atomization, rotating electrode and rotating coolant fluid techniques.

The catalyst alloy powder produced by atomization should preferably have a specific surface area of 0.01 to 1.0 m²/g, more preferably 0.01 to 0.5 m²/g, and especially 0.03 to 0.35 m²/g, as measured by the BET or air permeability method. Reactivity gives preference to an average particle size in the range of 1 to 200 μm, more preferably 3 to 100 μm, and most preferably 10 to 70 μm, as measured by laser diffraction particle size distribution analysis.

To improve the productivity of organohalosilanes, the catalyst alloy powder produced by atomization is desirably used in an effective amount relative to the total amount of silicon and depending on the reaction time, scale and metallic silicon grade. The effective amount is preferably 0.01 to 5% by weight, more preferably 0.05 to 3% by weight based on the contact mass.

In the step of heating the contact mass or imparting catalytic activity to the contact mass, an inert gas is used for fluidizing the contact mass in the reactor. Such an inert gas may be nitrogen or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas.

After the contact mass is heated to the reaction temperature or given catalytic activity as mentioned above, the organohalide is introduced into the reactor where gas-solid catalytic reaction takes place between the organohalide and silicon to form organohalosilanes. The conditions for this gas-solid catalytic reaction may be as in the conventional Rochow method. For example, the reaction is preferably effected at a temperature of about 250 to 600° C., and especially about 350 to 500° C.

The above reaction forms organohalosilanes of the general formula (I):

$$R_k(H)_m SiX_{(4-k-m)} \qquad (I)$$

wherein R is a monovalent $C_1$–$C_{12}$ hydrocarbon group, X is a halogen atom, k is an integer of 1 to 3, m is an integer of 0 to 2, preferably 0 or 1, and k+m is an integer of 1 to 3. It is preferred from the demand balance that m be approximately zero and k be approximately 1 to 2, both on the average. Then there is obtained a product containing a larger proportion, typically 50 to 95%, of diorganodihalosilane (D) wherein k=2 and m=0 which is most useful as the source to silicones and a less proportion of organotrihalosilane (T) wherein m=0. In ideal reaction conditions that avoid contact with Lewis acid such as ferric chloride, for example, a T/D ratio of typically 0.3 or less, and especially 0.1 or less is achievable.

EXAMPLE

Examples of the invention are given below by way of illustration and not by way of limitation. All parts and percents are by weight unless otherwise stated. The average particle size was measured by a particle size distribution analyzer based on the laser diffraction method. The BET specific surface area was determined by multi-point plotting based on nitrogen adsorption. An average value of the cumulative content of useful silane was determined by gas chromatography.

It is noted that all the catalyst alloys used in Examples were powdered by gas atomization.

Example 1

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of an atomized alloy powder of the composition: 91.6% Cu, 0.35% Sn and 8.05% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 2

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of an atomized alloy powder of the composition: 91.6% Cu, 0.35% Sn and 8.05% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 3

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of an atomized alloy powder of the composition: 91.59% Cu, 0.46% Sn and 7.95% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 4

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of an atomized alloy powder of the composition: 91.59% Cu, 0.46% Sn and 7.95% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 5

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of an atomized alloy powder of the composition: 91.09% Cu, 0.58% Sn and 8.33% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 6

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of an atomized alloy powder of the composition: 91.09% Cu, 0.58% Sn and 8.33% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 7

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of an atomized alloy powder of the composition: 90.71% Cu, 0.70% Sn and 8.59% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 8

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of an atomized alloy powder of the composition: 90.71% Cu, 0.70% Sn and 8.59% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 9

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.05 part of an atomized alloy powder of the composition: 85.86% Cu, 5.78% Sn and 8.36% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 10

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.04 part of an atomized alloy powder of the composition: 85.86% Cu, 5.78% Sn and 8.36% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 11

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.05 part of an atomized alloy powder of the composition: 86.53% Cu, 6.17% Sn and 7.3% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 12

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.04 part of an atomized alloy powder of the composition: 86.53% Cu, 6.17% Sn and 7.3% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 13

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.25 part of an atomized alloy powder of the composition: 84.24% Cu, 0.92% Sn and 14.84% P. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Example 14

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.20 part of an atomized alloy powder of the composition: 84.24% Cu, 0.92% Sn and 14.84% P. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Comparative Example 1

A fluidized bed reactor of carbon steel having a diameter of 75 mm and a height of 900 mm was charged with 100 parts of metallic silicon powder and a catalyst mixture of 4 parts metallic copper powder, 0.2 part zinc and 0.1 part tin. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 36 hours. The run was repeated 4 times. Reported in Table 1 are the concentrations of impurities in the metallic silicon used, an average of silane formation rate from the start to the end of reaction, and an average of cumulative content of useful silane.

Comparative Example 2

A fluidized bed reactor of carbon steel having a diameter of 75 mm and a height of 900 mm was charged with 100 parts of metallic silicon powder and a catalyst mixture of 5 parts copper oxide powder, 0.2 part zinc and 0.1 part tin. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 36 hours. The run was repeated 2 times. Reported in Table 1 are the concentrations of impurities in the metallic silicon used, an average of silane formation rate from the start to the end of reaction, and an average of cumulative content of useful silane.

Comparative Example 3

A fluidized bed reactor of carbon steel having a diameter of 75 mm and a height of 900 mm was charged with 100 parts of metallic silicon powder, a catalyst mixture of 4 parts metallic copper powder, 0.2 part zinc and 0.1 part tin, and 0.5 part of phosphor bronze (7.53% Sn, 0.35% P) powdered by grinding. Then a gas mixture of methyl chloride and nitrogen was fed to the reactor at a flow rate of 14.4 Nl/min and the reactor was heated to an internal temperature of 310° C. whereupon reaction continued. The metallic silicon powder and the catalyst mixture were fed to the reactor column from its bottom so as to keep constant the amount of reaction medium within the column. The reaction was terminated after 15 hours. The run was repeated 2 times. Reported in Table 1 are the concentrations of impurities in the metallic silicon used, an average of silane formation rate from the start to the end of reaction, and an average of cumulative content of useful silane.

Comparative Example 4

A fluidized bed reactor of carbon steel having a diameter of 75 mm and a height of 900 mm was charged with 100 parts of metallic silicon powder, a catalyst mixture of 5 parts copper oxide powder, 0.2 part zinc and 0.1 part tin, and 0.4 part of phosphor bronze (15.40% Sn, 0.60% P) powdered by grinding. Then a gas mixture of methyl chloride and nitrogen was fed to the reactor at a flow rate of 14.4 Nl/min and the reactor was heated to an internal temperature of 320° C. whereupon reaction continued. The metallic silicon powder and the catalyst mixture were fed to the reactor column from its bottom so as to keep constant the amount of reaction medium within the column. The reaction was terminated after 15 hours. The run was repeated 2 times. Reported in Table 1 are the concentrations of impurities in the metallic silicon used, an average of silane formation rate from the start to the end of reaction, and an average of cumulative content of useful silane.

than as specifically described without departing from the scope of the appended claims.

The invention claimed is:

1. A process for preparing organohalosilanes having the general formula (I):

$$R_k(H)_m SiX_{(4-k-m)}$$

wherein R is a monovalent hydrocarbon group of 1 to 12 carbon atoms, X is a halogen atom, k is an integer of 1 to 3, m is an integer of 0 to 2, and the sum of k+m is 1 to 3, by reacting metallic silicon particles with an organohalide in the presence of a copper-containing catalyst, wherein a contact mass is composed of (i.) the metallic silicon and (ii.) a copper-containing catalyst component comprising metallic copper or a copper compound and optionally a co-catalyst selected from the group consisting a metallic zinc, zinc compounds, metallic tin, tin compounds, metallic antimony, antimony compounds, metallic aluminum, aluminum compounds, metallic phosphorus, and phosphorus compounds and (iii.) an effective amount of a catalyst alloy, containing 0.2 to

TABLE 1

| | Reaction temp. (° C.) | Fe (%) | Al (%) | Ca (%) | Catalyst alloy powder Type | Sn concentration (%) | P concentration (%) | Additive concentration (%/Si)[a] | BET surface area (m²/g) | Silane formation rate (g/h)[b] | Useful silane content (%)[c] |
|---|---|---|---|---|---|---|---|---|---|---|---|
| Example 1 | 310 | 0.27 | 0.13 | 0.06 | atomized alloy[1] | 0.35 | 8.05 | 0.50 | 0.12 | 603 | 90.6 |
| Example 2 | 320 | 0.27 | 0.14 | 0.06 | atomized alloy[1] | 0.35 | 8.05 | 0.40 | 0.12 | 576 | 88.3 |
| Example 3 | 310 | 0.25 | 0.17 | 0.06 | atomized alloy[2] | 0.46 | 7.95 | 0.50 | 0.11 | 611 | 91.4 |
| Example 4 | 320 | 0.26 | 0.16 | 0.07 | atomized alloy[2] | 0.46 | 7.95 | 0.40 | 0.11 | 574 | 88.6 |
| Example 5 | 310 | 0.28 | 0.18 | 0.07 | atomized alloy[3] | 0.58 | 8.33 | 0.50 | 0.09 | 639 | 90.1 |
| Example 6 | 320 | 0.27 | 0.16 | 0.07 | atomized alloy[3] | 0.58 | 8.33 | 0.40 | 0.09 | 555 | 87.3 |
| Example 7 | 310 | 0.28 | 0.15 | 0.06 | atomized alloy[4] | 0.70 | 8.59 | 0.50 | 0.11 | 710 | 90.9 |
| Example 8 | 320 | 0.27 | 0.14 | 0.08 | atomized alloy[4] | 0.70 | 8.59 | 0.40 | 0.11 | 631 | 89.0 |
| Example 9 | 310 | 0.28 | 0.13 | 0.06 | atomized alloy[5] | 5.78 | 8.36 | 0.05 | 0.12 | 650 | 90.3 |
| Example 10 | 320 | 0.27 | 0.17 | 0.06 | atomized alloy[5] | 5.78 | 8.36 | 0.04 | 0.12 | 588 | 89.2 |
| Example 11 | 310 | 0.27 | 0.13 | 0.07 | atomized alloy[6] | 6.17 | 7.3 | 0.05 | 0.08 | 644 | 89.7 |
| Example 12 | 320 | 0.26 | 0.14 | 0.07 | atomized alloy[6] | 6.17 | 7.3 | 0.04 | 0.08 | 590 | 88.2 |
| Example 13 | 310 | 0.26 | 0.17 | 0.08 | atomized alloy[7] | 0.92 | 14.84 | 0.25 | 0.09 | 530 | 90.4 |
| Example 14 | 320 | 0.26 | 0.17 | 0.08 | atomized alloy[7] | 0.92 | 14.84 | 0.20 | 0.09 | 439 | 88.8 |
| Comparative Example 1 | 310 | 0.25 | 0.14 | 0.06 | none | — | — | — | — | 311 | 85.8 |
| Comparative Example 2 | 320 | 0.27 | 0.15 | 0.07 | none | — | — | — | — | 299 | 83.9 |
| Comparative Example 3 | 310 | 0.28 | 0.14 | 0.06 | ground phosphor bronze[8] | 7.53 | 0.35 | 0.50 | 0.20 | 355 | 74.7 |
| Comparative Example 4 | 320 | 0.26 | 0.12 | 0.08 | ground phosphor bronze[9] | 15.40 | 0.60 | 0.40 | 0.20 | 325 | 70.1 |

[a]Concentration of additive (catalyst alloy powder) relative to silicon
[b,c]an average of four runs for Comparative Example 1 and an average of two runs for Comparative Examples 2–4 and Examples 1–14
[1]alloy powder of the composition: 91.6% Cu, 0.35% Sn and 8.05% P, as atomized, average particle size 29 μm
[2]alloy powder of the composition: 91.59% Cu, 0.46% Sn and 7.95% P, as atomized, average particle size 22 μm
[3]alloy powder of the composition: 91.09% Cu, 0.58% Sn and 8.33% P, as atomized, average particle size 33 μm
[4]alloy powder of the composition: 90.71% Cu, 0.70% Sn and 8.59% P, as atomized, average particle size 31 μm
[5]alloy powder of the composition: 85.86% Cu, 5.78% Sn and 8.36% P, as atomized, average particle size 38 μm
[6]alloy powder of the composition: 86.53% Cu, 6.17% Sn and 7.3% P, as atomized, average particle size 47 μm
[7]alloy powder of the composition: 84.24% Cu, 0.92% Sn and 14.84% P, as atomized, average particle size 44 μm
[8]average particle size 55 μm
[9]average particle size 71 μm Japanese Patent Application No. 2004-077901 is incorporated herein by reference.

Although some preferred embodiments have been described, many modifications and variations may be made thereto in light of the above teachings. It is therefore to be understood that the invention may be practiced otherwise 8% by weight of tin, 4 to 20% by weight of phosphorus, and the balance of copper, which is powdered by atomization.

2. The process of claim 1, wherein the atomization is selected from the group consisting of gas atomization, vacuum atomization, water atomization, centrifugal atomization, rotating electrode and rotating coolant fluid techniques.

3. The process of claim 1, wherein the powdered catalyst alloy has an average particle size of 1 to 200 μm.

4. The process of claim 1, wherein the powdered catalyst alloy has a specific surface area of 0.01 to 1.0 m$^2$/g as measured by the BET or air permeability method.

5. A process for preparing organohalosilanes having the general formula (I):

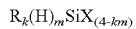

wherein R is a monovalent hydrocarbon group of 1 to 12 carbon atoms, X is a halogen atom, k is an integer of 1 to 3, m is an integer of 0 to 2, and the sum of k+m is 1 to 3, by reacting metallic silicon particles with an organohalide in the presence of a copper-containing catalyst, wherein a contact mass is composed of (i.) the metallic silicon and (ii.) a copper-containing catalyst component comprising metallic copper and optionally a co-catalyst selected from the group consisting a metallic zinc, zinc compounds, metallic tin, tin compounds, metallic antimony, antimony compounds, metallic aluminum, aluminum compounds, metallic phosphorus, and phosphorus compounds and (iii.) an effective amount of a catalyst alloy, containing 0.2 to 8% by weight of tin, 4 to 20% by weight of phosphorus, and the balance of copper, which is powdered by atomization.

* * * * *